United States Patent
Spahn

(10) Patent No.: US 7,355,183 B2
(45) Date of Patent: Apr. 8, 2008

(54) IMAGING DEVICE

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 426 days.

(21) Appl. No.: 11/035,713

(22) Filed: Jan. 15, 2005

(65) Prior Publication Data

US 2005/0161610 A1  Jul. 28, 2005

(30) Foreign Application Priority Data

Jan. 26, 2004  (DE)  ................ 10 2004 003 881

(51) Int. Cl.
*G06K 1/00* (2006.01)
*G01N 23/04* (2006.01)
*G01D 18/00* (2006.01)

(52) U.S. Cl. ................ 250/370.09; 378/62; 250/252.1

(58) Field of Classification Search ............ 250/252.1, 250/339.09, 370.09; 378/207, 62; 382/299, 382/275, 270, 132
See application file for complete search history.

(56) References Cited

U.S. PATENT DOCUMENTS

| 5,617,461 | A | 4/1997 | Schreiner |
| 6,034,794 | A * | 3/2000 | Suganuma ............ 358/518 |
| 6,222,901 | B1 * | 4/2001 | Meulenbrugge et al. ...... 378/19 |
| 6,350,985 | B1 * | 2/2002 | Rodricks et al. ......... 250/252.1 |
| 6,359,965 | B1 | 3/2002 | Finkler et al. |
| 6,381,374 | B1 * | 4/2002 | Pourjavid ............ 382/275 |
| 6,663,281 | B2 | 12/2003 | Aufrichtig et al. |
| 6,763,084 | B2 | 7/2004 | Boehm et al. |
| 6,819,786 | B2 * | 11/2004 | Hirai ............ 382/132 |

FOREIGN PATENT DOCUMENTS

| DE | 44 20 603 C1 | 6/1995 |
| DE | 195 27 148 C1 | 1/1997 |
| DE | 199 06 029 A1 | 8/2000 |
| DE | 199 34 980 A1 | 2/2001 |
| DE | 100 58 388 C1 | 8/2002 |
| DE | 101 22 876 A1 | 11/2002 |
| DE | 102 44 404 A1 | 5/2003 |
| EP | 0 857 983 A2 | 8/1998 |
| EP | 1 349 378 A1 | 10/2003 |

\* cited by examiner

*Primary Examiner*—David Porta
*Assistant Examiner*—Faye Boosalis

(57) ABSTRACT

In order to monitor an imaging device for x-ray machines it is proposed that reference system data (19) be recorded in conjunction with a calibration (16) or offset acquisition and that current comparison system data (20) be recorded later in the operating process, and that the performance of a new calibration (16) or the recording of a new offset image be triggered if the current comparison system data (20) deviates from the reference system data (19) by a predefined amount.

17 Claims, 2 Drawing Sheets

IMAGING DEVICE

CROSS REFERENCE TO RELATED APPLICATIONS

This application claims priority to the German application No. 10 2004 003 881.3, filed Jan. 26, 2004 which is incorporated by reference herein in its entirety.

FIELD OF INVENTION

The invention relates to an imaging device having a detector for recording high-energy images with the help of high-energy photons and having an evaluation unit which records the status of the system parameters describing the imaging device.

BACKGROUND OF INVENTION

Imaging devices of this type are generally known in the form of x-ray machines. X-ray machines for digital X-ray imaging are currently being developed. The new-style x-ray machines for digital x-ray imaging use so-called flat-panel detectors (among other things) that can be classified as flat-panel detectors with direct conversion and flat-panel detectors with indirect conversion.

Flat-panel detectors with indirect conversion have a scintillator extended over the surface, which covers a read-out matrix made from amorphous silicon. Various materials may be used for the scintillator. Materials normally used are manufactured on the basis of CsI or $Gd_2O_2S$. The read-out matrix comprises a plurality of photodiodes which convert the light generated in the scintillator from incident x-rays into electrical charges. These electrical charges are stored in capacitors allocated to each of the individual photodiodes, and, after the recording process is complete, are read out by active switching elements and converted into digital data with the help of analog-digital converters.

In flat-panel detectors with direct conversion, the incident x-rays are converted into electrical charges in a photoconductive layer, which is typically made from amorphous selenium, stored in electrodes adjoining the photoconductive layer, and then read out from the electrodes with the help of active switching elements.

SUMMARY OF INVENTION

The digital data generated with the new-style flat-panel detectors cannot be used for diagnostic purposes in its raw state, since the optical and electrical properties of the individual detector elements of the flat-panel detectors, the pixels, can vary greatly. For example, the individual photodiodes, switching transistors and switching diodes have different sensitivity levels and electrical properties, in particular different leakage currents. In addition, the resistance values and capacity values may turn out differently from row to row, from column to column, or from pixel to pixel, even from the point of manufacture. Even the individual inputs of the booster chips used for reading out the photodiodes or electrodes may vary in their properties.

Particularly significant are the differences in flat-panel detectors that consist of a plurality of individual partial matrices arranged adjacent to one another, since the optical and electrical properties of the individual partial matrices may vary greatly. These partial matrices may each be separately manufactured amorphous silicon plates or may be produced by subdividing the circuitry of the readout matrix, by allocation of the various detector areas to different chips of the readout and control electronics.

For these and other reasons it is necessary for calibrations and offset acquisitions to be carried out at regular intervals.

In offset acquisition for the purpose of obtaining offset images, darkframes are usually recorded at intervals ranging from milliseconds to minutes in order to obtain offset images. This is because the offset is essentially determined by leak age currents, which are heavily dependent on the detector temperature. The leakage currents may result in rapid fluctuations since the detector temperature—for its part—depends on the ambient temperature and on temperature fluctuations occurring during operation due to power dissipation.

A further reason for performing offset acquisition is that it enables ghost image artifacts to be corrected. In flat screen detectors, x-ray images normally leave retained images, which usually fade away exponentially. The retained images have typically disappeared after about 10 to 30 seconds. There are however medical applications in which an x-ray image must be taken roughly every 30 milliseconds. Examples include recording processes with x-ray photons in various energy fields, whole-body images in which individual x-ray images are assembled, or even straightforward thoracic x-rays.

In contrast to offset acquisitions, calibrations are carried out at intervals of days, weeks or even months, since the data obtained by them still reflects the current status of the imaging device with sufficient accuracy, even after these timespans.

In order to carry out a calibration it is necessary to record a plurality of x-ray images under different exposure conditions. The x-ray images are subsequently processed into so-called gain images and so-called defect images, whereby the offsets are extracted from the raw data and the sensitivity levels of the individual pixels are determined. The gain images then reflect the sensitivity of the individual detector elements, whilst the defect images show the detector elements that have failed completely or are behaving atypically. A calibration normally takes about one hour to carry out and generally requires the presence of staff.

The performance of calibration and offset acquisition is also referred to below as production of correction images. The correction images generated during calibration or offset acquisition are then used in an image-processing unit in order to generate, from the raw digital data, x-ray images that are free from artifacts and suitable for diagnostic purposes.

Correction images should always be generated as frequently as possible to ensure that the correction image describes the current status of the imaging device. On the other hand, recording a correction image is time-consuming and interrupts the work routine.

It is therefore an object of the invention to create an imaging device that delivers good-quality, high-energy images of the objects to be imaged, and whose operation is interrupted as little as possible by the production of correction images.

This object is achieved the claims. Advantageous embodiments and developments are described in the dependent claims.

In the imaging device, the evaluation unit records—in conjunction with the production of a correction image—a system parameter that describes the status of the imaging device. The imaging device also monitors the development of this system parameter over time and requests the production of a new correction image if a predefined threshold value is exceeded. The correction images are therefore only generated if the value of the monitored system parameter varies significantly compared to the value of the system parameter for the period in which the last correction image was produced. The correction images are therefore only generated if a new correction image needs to be produced because a significant change in the monitored system parameter is suspected. The production of correction images is therefore carried out according to demand. As a result, the production of correction images takes up only as much time as is necessary, and consequently the work routine is impaired as little as possible.

In a preferred embodiment the imaging device incorporates a detector with indirect conversion and also a radiation source for low-energy photons that can be applied to the detector. With the help of the low-energy photons, further low-energy images can be taken in conjunction with a calibration operation. The recording of low-energy images can then be repeated at brief intervals after the calibration is completed. By evaluating the successively recorded low-energy images, the status of the detector can be determined since the low-energy image shows the status of the read-out matrix and of the subsequent read-out electronics. Only the conversion of the high-energy radiation into low-energy light in the scintillator is not recorded. If the evaluation indicates that a new calibration needs to be performed, the evaluation unit signals that a new correction image is being recorded.

In a further preferred embodiment the evaluation unit records, in conjunction with the production of a correction image, a defect image in the form of a darkframe and monitors the number of defects during the further operation.

In a further preferred embodiment the evaluation unit records—in conjunction with a calibration operation—the temperature of the detector. If subsequent monitoring indicates that the temperature of the detector has exceeded a defined threshold value, the evaluation unit requests the performance of a new calibration. Since the temperature of the detector significantly affects the boosting of the pixels in the detector, a reliable compensation of image artifacts may be achieved in this way.

In a further preferred embodiment the evaluation unit monitors—in conjunction with an offset acquisition operation—a dark reference zone of the offset-corrected high-energy image. Since, in a dark reference zone, the values of the high-energy image should be equal to the values of the offset image, the offset-corrected high-energy image would have to show only zero values. If the actual values exceed a predefined threshold, the evaluation unit triggers the generation of a new correction image, in this case the recording of an offset image.

In a further preferred embodiment the evaluation unit records—in conjunction with the performance of an offset acquisition operation—the temperature of the detector. If the subsequent monitoring indicates that the temperature of the detector has exceeded a defined threshold value, the evaluation unit requests the recording of a new offset image. Since the temperature of the detector significantly affects the offset of the pixels in the detector, a reliable compensation of the image artifacts may be achieved in this way.

Furthermore, it may be expedient to monitor the time that has elapsed since the last offset acquisition. This is to ensure that an erroneous offset image is not used for a prolonged period.

BRIEF DESCRIPTION OF THE DRAWINGS

Other features and advantages of the invention are explained in the following description, in which exemplary embodiments of the invention are described in detail with the help of the attached diagrams. In these diagrams.

DETAILED DESCRIPTION OF INVENTION

Figure 1:
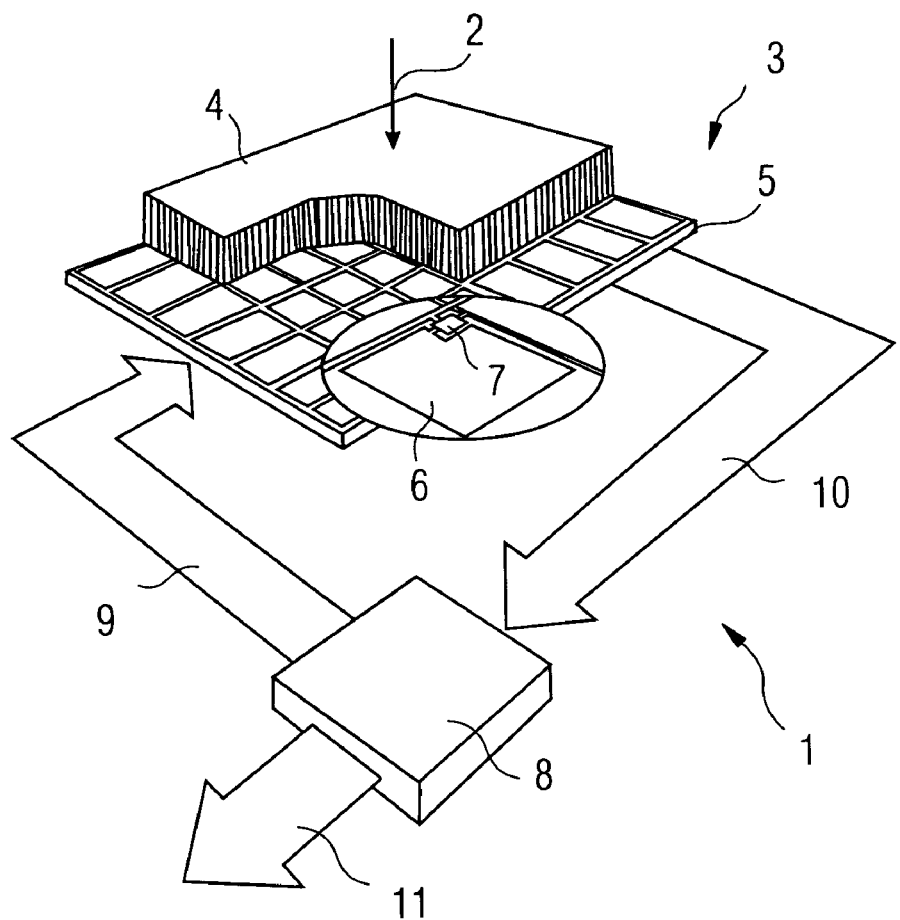
FIG. 1 is a perspective view of an imaging device, with a partially cut-away flat-panel detector with indirect conversion.

FIG. 1 shows an imaging device 1, which is p art of an x-ray device and which incorporates an x-ray source (not shown in FIG. 1) for generating x-rays 2. The x-rays 2 fall on a flat-panel detector 3 after passing through an object to be radiographed. The flat-panel detector 3 typically measures about 30 cm by 30 cm. The flat-panel detector 3 incorporates a scintillator 4, which is manufactured—for example—from CsI. Below the scintillator 4, there is an active matrix 5, which is normally manufactured on the basis of amorphous silicon. A field of photodiodes is formed on the active matrix 5. In the photodiodes 6, the light generated in the scintillator 4 via the respective photodiode 6 is absorbed. During this absorption, electron-hole pairs are generated which migrate in turn to the anode and cathode of the respective photodiode 6. The charge thus generated is stored in the respective photodiode 6 until said photodiode 6 is read out with the help of an active switching element 7. The active switching elements 7 are activated in rows by an evaluation unit 8 via address lines 9. The charge stored in the photodiodes 6 is read out column-by-column via data lines 10.

It should be expressly noted that the term evaluation unit 8 describes the function of the said unit. The evaluation unit 8 does not necessarily have to be implemented in a separate semiconductor element. The evaluation unit 8 might rather incorporate a plurality of semiconductor elements from one or more printed circuit boards. The evaluation unit 8 may also include functional groups in different devices. The purpose of the evaluation unit 8 is to control and monitor the flat-panel detector 3. The evaluation unit 8 may also have the task of generating, from the raw digital data, a digital x-ray image 11 suitable for diagnostic purposes, and outputting this image on a display unit 1 (not shown in FIG. 1).

Figure 2:
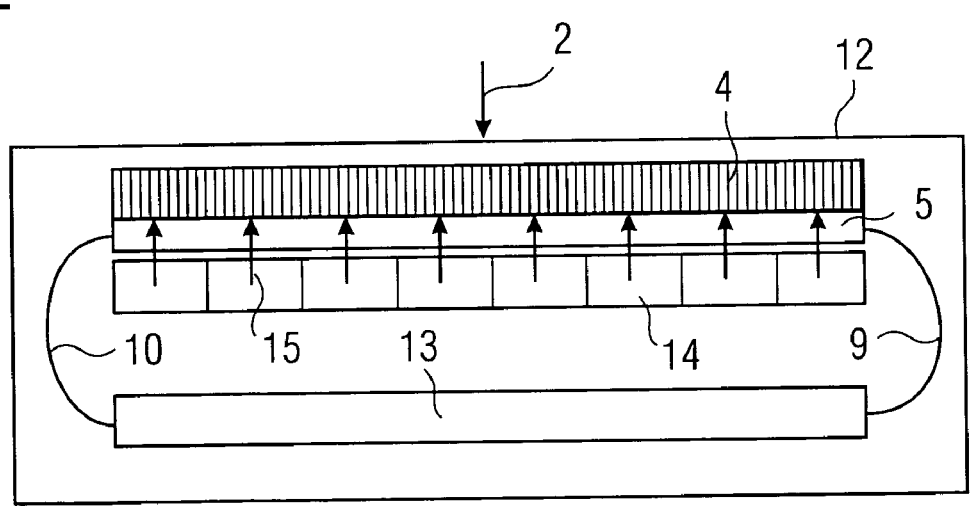
FIG. 2 is a cross-section through the imaging device from FIG. 1.

FIG. 2 shows a cross-section through the mechanical structure of the imaging device 1 from FIG. 1. The scintillator 4, which rests on the active matrix 5, is located in a housing 12. The active matrix 5 is connected via the address lines 9 and the data lines 10 to a printed circuit board 13, on which are arranged functional modules of the evaluation unit 8. Between the printed circuit board 13 and the active matrix 5 is located a reset light source 14, which emits light 15 in the optical wavelength range toward the active matrix 5. The reset light source 14 is used to generate continuously, in the photodiodes 6 of the active matrix 5, electron-hole pairs through which so-called deep traps are held in saturation. As a result, the dark current is not just particularly distinctive in those areas of the flat-panel detector 3 that were exposed to the x-rays 2. Instead, said dark current is applied homogeneously over the flat-panel detector 3. These measures enable the retained images—otherwise known as ghost defects—to be significantly reduced, since the dark current generated by the disintegration of the deep traps is applied evenly across the flat-panel detector 3 and not just in the areas of the flat-panel detector 3 that are exposed to x-rays 2.

The flat-panel detector must be calibrated with regard to the sensitivity of the individual detector elements, the so-called "gain", since the sensitivity of the photodiodes 6 of the currently active switching elements 7 of the electronics connected in series may turn out to be different. The differences are particularly great if the flat-panel detector 3 has an active matrix 5 assembled from several submatrices.

In addition, the thickness and the material characteristics of the scintillator 4 may vary, resulting in differences in efficiency in the conversion of the x-rays 2 into optical light. The detector elements of the flat-panel detector 3, that are defined by the dimensions of the photodiodes 6, thus vary in their sensitivity. It is therefore necessary for the relative sensitivity of the detector elements to one another to be defined by means of calibration, and for this relative sensitivity to be taken into account when the raw digital data is converted into the finished x-ray image.

It is also possible for individual detector elements to fail completely or to behave atypically. The defective or atypically behaving detector elements are recorded in a defect image. This defect image is likewise taken into account when the raw digital data is converted into the finished x-ray image.

The production of the defect image and the determination of the relative sensitivity of the individual detector elements for a gain image are referred to below simply as calibration.

Figure 3:
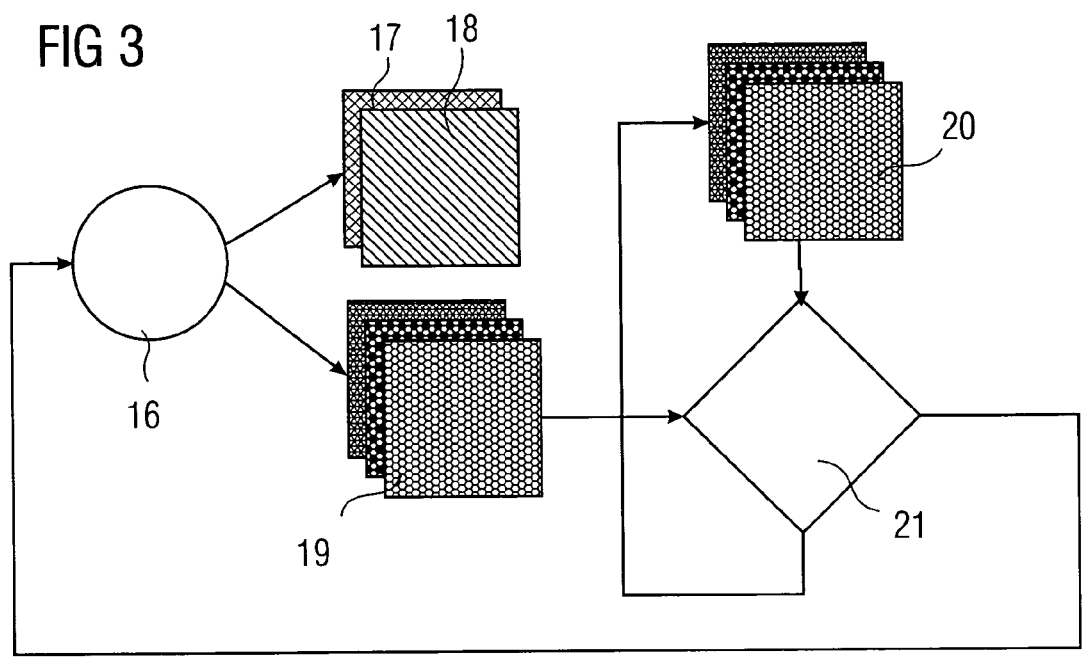
FIG. 3 is a diagram showing the working stages executed during monitoring of the calibration of a flat-panel detector.

FIG. 3 shows a flow chart of a monitoring process carried out by the evaluation unit 8 on the flat-panel detector 3, by which the time of a new calibration is determined. According to the flow chart shown in FIG. 3, a current calibration 16 is carried out first. The actual calibration data thus obtained incorporates a gain image 17 and a defect image 18. Reference system data 19, which is used as the reference later in the process and is described in greater detail below, is also recorded during the current calibration 16. The recording of reference system data 19 is carried out as near as possible to the time at which the gain image 17 and the defect image 18 are produced.

Later in the operating process of the imaging device 1, current comparison system data 20 is obtained and compared to the reference system data 19 in an arithmetic unit 21. On the basis of predefined threshold values, the arithmetic unit 21 decides whether a new calibration 16 is necessary or whether the monitoring is to be continued without calibration 16, by recording current system data 20 again after a defined period of time.

Different types of data may be used as reference system data 19 and as comparison system data 20.

So-called reset light images are particularly suitable for this purpose. Reset light images are images in which the active matrix 5 is illuminated by the reset light source 14. The reset light images are then generated, whereby a current offset image is taken from the raw data read out from the active matrix 5.

The reset light resemble an x-ray image with homogeneous exposure, since the entire conversion chain—from the conversion of the optical photons into charge in the photodiodes 6, to the further process stages of boosting, multiplexing and digital conversion—is carried out up to the conversion of the x-rays 2 into optical light in the scintillator 4. The reset light images therefore correspond as closely as possible to those having gain images generated with x-rays 2 and are therefore a good basis on which to decide whether or not the gain images is to be updated.

The reset light images also accurately reflect the defect situation, since only defects that are related to the scintillator 4 are not recorded.

Reset light images may sometimes be produced with varying exposure conditions in order to monitor the flat-panel detector 3 in different dynamic areas.

The reset light images can be analyzed in the arithmetic unit 21 by various methods. For example, the quotient from a reference reset light image and a comparison reset light image can be calculated, after which the generation of a new gain image will always be triggered if the mean values of the quotient image deviate from the value 1 by a predefined percentage, for example two percent, or if the noise in the quotient image exceeds a predefined value, or if the mean values in one or more predefined regions in the quotient image deviate from one another by more than a certain percentage.

The defect images can also be used as reference system data 19 and as system data 20. For example, defect images that can be used as comparison system data 20, can be generated in the background without incident x-rays 2. This reference system data may be compared to a defect image that shows the reference system data 19, said defect image having been recorded, without x-rays 2, in conjunction with the calibration of the flat-panel detector 3. The arithmetic unit 21 may be set so that a new calibration is requested whenever the number of defects in the two defect images exceeds a predefined percentage, for example 2 percent, or is higher than an absolute figure, for example 5 defects.

The temperature values of the flat-panel detector 3 that are recorded in conjunction with a calibration can also be used as reference system data 19. If the current temperature of the flat-panel detector 3 then deviates from the reference temperature by more than a predefined temperature variation—e.g. 5° Celsius—for example due to a seasonal increase in temperature, the arithmetic unit 21 may then request a new calibration.

In a modified embodiment the arithmetic unit 21 is able not only to trigger the new calibration 16 or make staff aware of the need for a new calibration, but also to request a maintenance engineer. This may be necessary, for example, if the deviation of the comparison system data 20 from the reference system data 19 is large enough to indicate the presence of a fault in the imaging device 1, and that the latter can no longer be calibrated. The request for a maintenance engineer may be displayed to the user on the control monitor, for example, or may also be implemented automatically, for example by an e-mail via a data network.

The imaging device 1 described with the help of FIGS. 1 to 3 also supports the initial case following a reinstallation, if the initial reference system data 19 is set to atypical values, for example zero, and therefore automatically shows a considerable deviation compared to the current comparison system data 20. In this case a calibration is requested immediately after commissioning.

The imaging device 1 has the advantage that the comparison system data can always be generated in the background without x-rays 2. The comparison system data 20 can therefore be generated regularly while the imaging device 1 is not being used, for example at night or between two patients.

Figure 4:
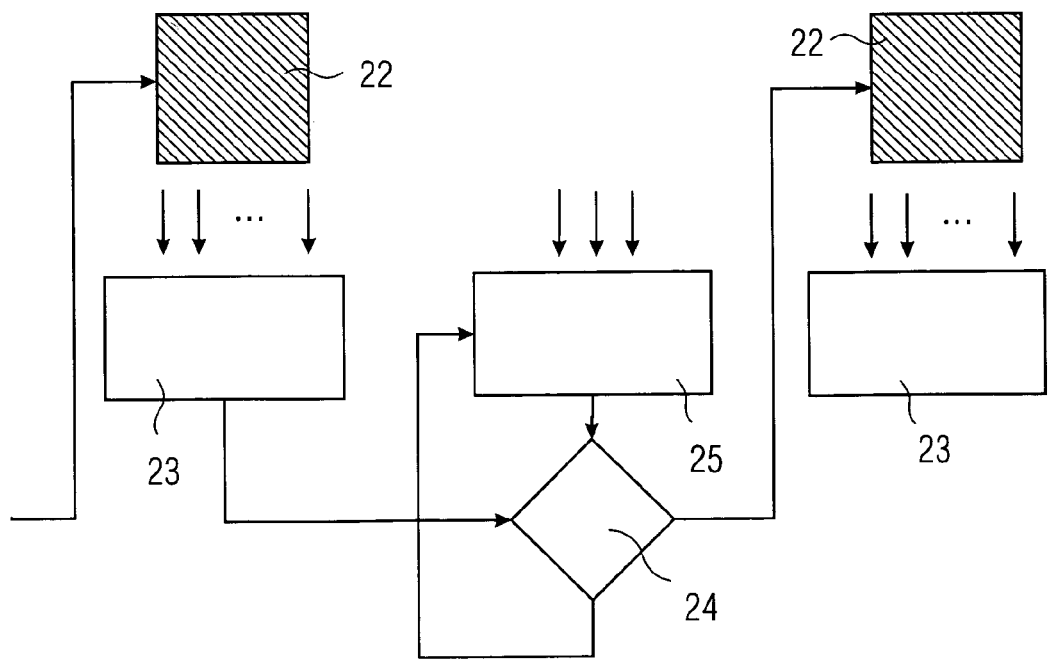
FIG. 4 a flow-chart showing the working stages carried out during monitoring of the offset acquisition.

The imaging device 1 according to FIG. 4 is also able to carry out the offset acquisition operation on a demand-led basis. According to FIG. 4, reference system data 23 is recorded at around the same time as the recording of an offset image 22, and said reference data is then compared to current comparison system data 25 in an arithmetic unit 24. Since the offsets of the individual detector elements of the flat-panel detector 3 are dependent on operating parameters such as the x-ray window length, the image frequency or retained images of previous x-rays, the offsets of the detector elements of the flat-panel detector 3 must be monitored with roughly the same frequency as the recording of the x-ray images.

Different types of data can be used for the reference system data 23 and the comparison system data 25.

In one exemplary embodiment, for example, the current temperature of the flat-panel detector 3 is read out once per second. This temperature is compared with the temperature that was measured immediately before the acquisition of the last offset image 22. If the current temperature falls above or below the reference temperature by a defined threshold value, for example 1° Celsius, the acquisition of a current offset image 26 is triggered. As soon as the imaging device 1 is able to do so, the new offset image 26 is recorded and used thereafter for subsequent offset corrections.

In a modified exemplary embodiment a linear combination of the current offset image 26 with the previous offset image 22 is used to correct the offset. This measure makes it possible to improve the offset correction of x-ray images that are recorded in the period between the recording of the two offset images 26 and 26.

In a further modified embodiment, it is also possible to use—in addition to the temperature of the flat-panel detector 3—the time that has elapsed since the recording of the last offset image 22, as a factor in determining whether a new offset image 26 is to be acquired. For example, an upper threshold value can be defined for the maximum permissible timespan between the acquisition of two offset images. For example, it could be possible to require that no more than five minutes may elapse between the recording of the two offset images 22 and 26. It is also possible, in this connection, to use a linear combination of the two offset images 22 and 26 to correct the offset.

In a further embodiment, the arithmetic unit 24 may subject the offset-corrected x-ray image 11 to image analysis. The x-ray image 11 may, for example, have a so-called dark reference zone, on which no x-rays fall and in which, therefore, no x-ray signal is generated. In the dark reference zone, the raw digital data is the same as the offset image data since only leakage currents and similar effects are recorded, but not signals created by x-rays. The digital values of the offset-corrected x-ray image 11 would therefore have to be zero in the dark reference zone. The arithmetic unit 24 can therefore be set such that the recording of a new offset image 26 is only triggered if the values of the x-ray image 11 fall above or below a predefined value in the dark reference zone.

In a further modified embodiment, two or three of the system parameters described here can be used to trigger the acquisition of a new offset image 26. For example, the acquisition of the new offset image 26 can be triggered whenever one of the three comparison processes makes the acquisition of the new offset image 26 necessary. In another case the acquisition of the new offset image 26 is carried out whenever this is demanded by two or all three comparison processes.

The acquisition of the offset images 22 and 26 as described here offers the advantage that it is only carried out if required, and therefore the work routine is only interrupted insofar as is necessary. This is particularly advantageous if images are to be recorded in rapid succession.

It should be noted that system parameters other than the ones described here may also be used to determine whether a calibration or offset image acquisition is to be carried out. All system parameters that affect the calibration and the offset behavior of the imaging device 1 may be used for this purpose.

It should further be noted that the threshold value with which the current system parameter in question is compared is not necessarily the same for all operating modes. Instead, different threshold values may be used depending on the operating mode.

The invention claimed is:

1. An imaging device, comprising:
   a detector for recording a high-energy image using high-energy photons; and
   an evaluation unit for recording a system parameter representing a status of the imaging device, wherein the evaluation unit is adapted to:
   acquire a current value of the system parameter related to generating a correction image while processing the high-energy image;
   monitor a development of the current value of system parameter over time; and
   trigger a generation of an updated correction image if the current value of the system parameter violates a parameter limit value.

2. The imaging device according to claim 1, wherein the evaluation unit is further adapted to:
   acquire system reference data during a calibration operation of the imaging system;
   acquire system comparison data during a subsequent operation of the imaging device; and
   trigger a new calibration operation of the imaging system if the system comparison data deviate from the system reference data by more than a data limit value.

3. The imaging device according to claim 2, wherein the imaging device further comprises a radiation source for emitting low-energy photons, and the system reference data and the system comparison data are low-energy images recorded by utilizing low-energy photons emitted from the radiation source.

4. The imaging device according to claim 3, wherein the evaluation unit is further adapted to calculate a quotient image using a low-energy reference image and a low-energy comparison image.

5. The imaging device according to claim 4, wherein the evaluation unit is adapted to trigger the new calibration operation if a mean value of the quotient image exceeds a limit quotient value.

6. The imaging device according to claim 4, wherein the evaluation unit is adapted to trigger the new calibration operation if a calculated noise data value based on the quotient image exceeds a noise data limit value.

7. The imaging device according to claim 4, wherein the evaluation unit is adapted to trigger the new calibration operation if a first and a second area of the quotient image deviate from each other by more than an area deviation limit value.

8. The imaging device according to claim 2, wherein the system reference data and the system comparison data is selected form the group consisting of: a reset light image, a defect image, and a temperature value of the detector.

9. The imaging device according to claim 8, wherein the system comparison data is acquired after a defined period of time.

10. The imaging device according to claim 8, wherein the evaluation unit requests a maintenance engineer if a deviation of the system comparison data from the system reference data is large enough to indicate a fault in the image device.

11. The imaging device according to claim 1, wherein the evaluation unit is further adapted to:
record a defect reference image during a calibration operation of the imaging device;
record a comparison defect comparison image during a subsequent operation of the imaging device; and
trigger a new calibration operation if the defect comparison image deviates from the defect reference image by more than a defect limit value.

12. The imaging device according to claim 1, wherein the evaluation unit is further adapted to:
acquire a reference temperature of the detector during a calibration operation of the imaging device;
acquire a comparison temperature of the detector during a subsequent operation of the imaging device; and
trigger a new calibration operation if the comparison temperature deviates from the reference temperature by more than a temperature limit value.

13. The imaging device according to claim 1, wherein the evaluation unit is further adapted to:
acquire system reference data during a recording process of an offset image;
acquire system comparison data during a subsequent operation of the imaging device; and
trigger a new recording process of a previously presented offset image if the system comparison data deviate from the system reference data by more than an offset limit value.

14. The imaging device according to claim 13, the system reference data and the system comparison data represent temperature values related to the detector.

15. The imaging device according to claim 13, wherein the system reference data and the system comparison data represent system time values of the imaging device.

16. The imaging device according to claim 13, wherein the system reference data and the system comparison data correspond to image data of an offset-corrected high-energy image related to a dark area of high-energy images.

17. The imaging device according claim 13, further comprising an image processing unit adapted to process linear combinations of offset images for correcting the high-energy image.

* * * * *